(12) United States Patent
Hingley et al.

(10) Patent No.: US 10,702,880 B2
(45) Date of Patent: Jul. 7, 2020

(54) LIQUID LEVEL SENSOR

(71) Applicant: Saban Ventures PTY Limited, Alexandria (AU)

(72) Inventors: Brian Hingley, Sydney (AU); Michael Potas, Sydney (AU)

(73) Assignee: Saban Ventures PTY Limited, Alexandria (AU)

( * ) Notice: Subject to any disclaimer, the term of this patent is extended or adjusted under 35 U.S.C. 154(b) by 0 days.

(21) Appl. No.: 16/009,481

(22) Filed: Jun. 15, 2018

(65) Prior Publication Data

US 2018/0290166 A1  Oct. 11, 2018

Related U.S. Application Data

(62) Division of application No. 14/128,258, filed as application No. PCT/AU2012/000735 on Jun. 25, 2012, now abandoned.

(30) Foreign Application Priority Data

Jun. 24, 2011  (AU) ............................... 2011902486

(51) Int. Cl.
    *B05B 12/08* (2006.01)
    *G01F 23/26* (2006.01)
    (Continued)

(52) U.S. Cl.
    CPC ......... *B05B 12/081* (2013.01); *A61M 11/005* (2013.01); *G01F 23/241* (2013.01);
    (Continued)

(58) Field of Classification Search
CPC ..... B05B 12/08; B05B 12/081; G01F 23/261; G01F 23/265; A61L 2/22
(Continued)

(56) References Cited

U.S. PATENT DOCUMENTS 4,507,521 A    3/1985   Goellner
4,749,988 A    6/1988   Berman et al.
(Continued)

FOREIGN PATENT DOCUMENTS

DE      3025982 A1    1/1982
DE      3710141 A1    10/1988
(Continued)

OTHER PUBLICATIONS

English translation of DE3710141. IDS provided by the Applicant on Jun. 28, 2018. By Kohler. (Year: 1988).*
(Continued)

*Primary Examiner* — Chee-Chong Lee
(74) *Attorney, Agent, or Firm* — Stinson LLP

(57) ABSTRACT

A nebuliser cup for maintaining a safe level of liquid during nebulization, the cup comprising a liquid level sensor comprising: a first element sensing liquid at or below a position corresponding to a filled liquid level in the nebuliser cup; a second element electrically isolated from the first element and located at a position corresponding to a filled liquid level in the nebuliser cup; and wherein when the cup is not filled with a liquid to the filled liquid level, the first element, the liquid and the second element do not form an electrically coupled circuit; and when the cup is filled with a liquid to the filled to liquid level, the first element, the liquid and the second element together form an electrically coupled circuit.

14 Claims, 6 Drawing Sheets

Figure 1:
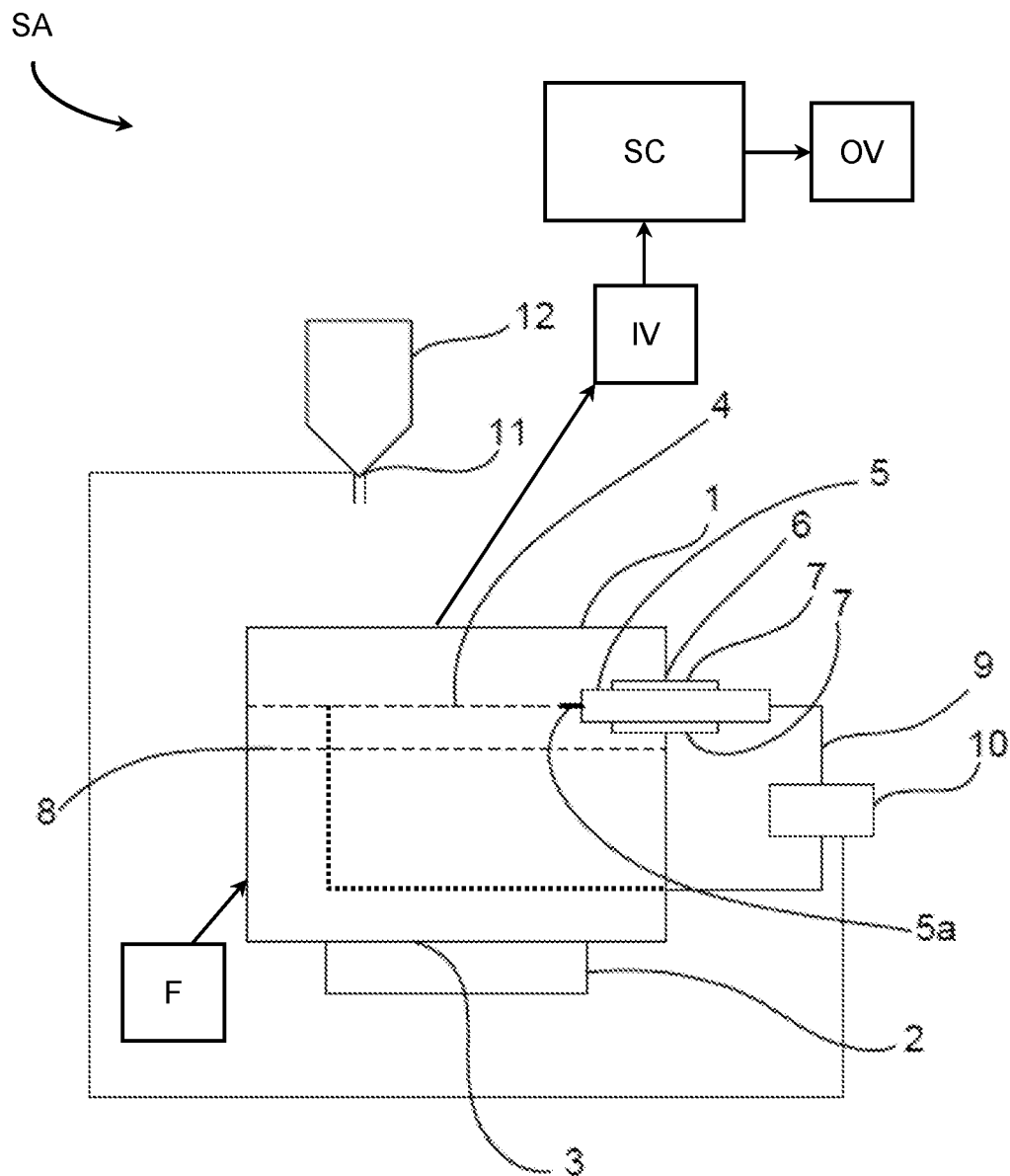

(51) Int. Cl.
 *A61M 11/00* (2006.01)
 *G01F 23/24* (2006.01)
 *B05B 17/06* (2006.01)
 *A61L 2/22* (2006.01)

(52) U.S. Cl.
 CPC .......... *G01F 23/242* (2013.01); *G01F 23/261* (2013.01); *G01F 23/265* (2013.01); *A61L 2/22* (2013.01); *A61M 2202/20* (2013.01); *B05B 17/0615* (2013.01)

(58) Field of Classification Search
 USPC ...................................................... 239/102.2
 See application file for complete search history.

(56) References Cited

U.S. PATENT DOCUMENTS

| | | | |
|---|---|---|---|
| 5,277,175 | A | 1/1994 | Riggs et al. |
| 5,477,727 | A | 12/1995 | Koga |
| 5,726,908 | A | 3/1998 | Hosmer et al. |
| 6,028,521 | A | 2/2000 | Issachar |
| 6,684,609 | B1 | 2/2004 | Bassissi et al. |
| 7,509,856 | B1 | 3/2009 | Winkens et al. |
| 7,628,339 | B2 | 12/2009 | Ivri et al. |
| 2003/0000303 | A1 | 1/2003 | Livingston et al. |
| 2004/0226894 | A1* | 11/2004 | Okazaki ................ A01N 59/00 210/756 |
| 2005/0045621 | A1 | 3/2005 | Chenier et al. |
| 2007/0277816 | A1 | 12/2007 | Morrison et al. |
| 2008/0223404 | A1 | 9/2008 | Erickson |
| 2009/0031798 | A1 | 2/2009 | Radhakrishnan et al. |
| 2009/0158841 | A1 | 6/2009 | Winkens |
| 2009/0314798 | A1 | 12/2009 | Hovinen et al. |
| 2010/0224697 | A1 | 9/2010 | Modlin et al. |
| 2010/0231393 | A1 | 9/2010 | Sherron |
| 2013/0026250 | A1 | 1/2013 | Burt et al. |
| 2013/0042642 | A1* | 2/2013 | Ferreira ................ C02F 3/1221 62/264 |

FOREIGN PATENT DOCUMENTS

| | | |
|---|---|---|
| JP | S63-210541 A | 9/1988 |
| JP | H07-016122 U | 1/1995 |
| JP | 10-281853 A | 10/1998 |
| RU | 2000810 C1 | 10/1993 |
| WO | 2007/014435 A1 | 2/2007 |

OTHER PUBLICATIONS

English Abstract of JP 56030545, 1981 (1 page).
English Abstract of JP 63210541, 1987 (1 page).
International Search Report, PCT/AU2012/000735, dated Sep. 26, 2012, 8 pages.
International-Type Search Report, Australian National Application No. 2011902486, dated Sep. 6, 2011, 3 pages.

* cited by examiner

LIQUID LEVEL SENSOR

REFERENCE TO RELATED APPLICATIONS

This application is a division of U.S. patent application Ser. No. 14/128,258, filed Feb. 24, 2014, which is the U.S. National Stage Application of International Application No. PCT/AU2012/000735, filed Jun. 25, 2012, and claims the benefit of Australian Patent Application No. 2011902486, filed Jun. 24, 2011, the entire disclosures of which are incorporated herein by reference.

FIELD OF THE INVENTION

The invention relates to methods and apparatus for sterilisation which employ the use of ultrasonic agitation of liquids to generate sterilising aerosols.

BACKGROUND OF THE INVENTION

Any discussion of the prior art throughout the specification should in no way be considered as an admission that such prior art is widely known or forms part of the common general knowledge in the field.

Sterilisers are used in the medical, food and packaging industries to kill and thereby prevent the transmission of transmissible agents such as spores, fungi, and bacteria. A typical steriliser creates a set of physical conditions in a sterilisation chamber that effectively kills nearly all of these transmissible agents.

Contacting articles in need of sterilisation with sterilant aerosols is one known method of sterilisation. Referring to FIG. 1, a typical aerosol sterilisation apparatus SA has a sterilisation chamber SC with inlet and an outlet valves (IV and OV, respectively), an aerosol generator 2 (typically a nebuliser) in fluid communication with the chamber via the inlet valve and a fan F upstream of, and in fluid communication with, the aerosol generator.

In use, an article requiring sterilisation is placed in the chamber, which is then sealed. The aerosol inlet valve is opened and the outlet valve is closed. The fan is engaged, which creates a gas stream through or the past the aerosol generator, into the chamber. A passive vent in the sterilisation chamber allows for pressure equalization as required, to permit gas flow in and out of the sterilisation chamber. The aerosol generator, which contains the desired sterilant, is then activated, putting a large number of small sterilant droplets into the gas stream. The droplets are carried by the gas stream to create an aerosol which travels into the sterilisation chamber. The sterilant then acts upon the contents of the chamber, killing pathogenic organisms as required.

One type of nebuliser which has proved to be well suited for sterilization applications is an ultrasonic nebuliser.

In an ultrasonic nebuliser, a sterilization liquid is placed in a cup which sits above and in contact with an ultrasonic transducer. Typically, the ultrasonic transducer is a piezo-electric crystal that changes size or shape in response to electrical stimulus. The application of alternating current to the crystal at high frequencies (of the order of several MHz) leads to the crystals vibrating at a corresponding frequency. This energy is in turn transferred to the sterilization liquid. The cup and transducer may typically be configured to focus the distribution of energy in the sterilization liquid. The energy causes small microdroplets to be formed from the liquid and become airborne. Typically, there are many such particles which together form a nebulant or mist of aerosol particles. This nebulant is then delivered to the sterilizing chamber.

One problem with such an arrangement is that if the sterilizing liquid is fully consumed and the cup becomes empty, then any continuing operation of the device is likely to result in damage—the energy is not dissipated by the nebulant, but rather is retained by the transducer and cup, causing the arrangement to overheat which can irreversibly damage the transducer unit, for example, by delamination or depolarisation of the transducer.

Another problem of such an arrangement is that if the sterilizing liquid overfills the cup, the transducer experiences an increase in load and the system efficiency can reduce, potentially causing an undersupply of sterilizing aerosol and a resulting failure to sterilize.

"Sterilization" is generally defined as a process capable of achieving a log 6 reduction in concentration of spores. "Disinfection" is a similar process, the difference being that it results in a lesser degree of biocidal effect. "Sterilization" includes "disinfection" and "disinfection/sterilization" is an abbreviation for "disinfection and/or sterilization". In the present application, "disinfection" and "sterilization" are used interchangeably.

Because of the constructional requirements of ultrasonic sterilizers, it is not a trivial task to in determine when there is an appropriate level of liquid in the ultrasonic cup. The sterilizing liquid usually contains hydrogen peroxide, which is highly toxic and corrosive, requiring the cup and the transducer to be maintained in a tightly sealed system. Any sensing means needs to be sufficiently robust to withstand repeated exposure to toxic and corrosive peroxide liquid and vapour, possibly at high temperatures. In addition, because of the fluid in the environment and the possibility of splashing, the sensor need to be highly accurate in its ability to avoid false positive and false negative results, which could lead to either destruction of the transducer element or an undersupply of sterilizing aerosol.

Thus, there is a need for sensor for determining the level of liquid in an ultrasonic cup which is robust enough to endure repeated exposure to sterilization conditions.

SUMMARY OF THE INVENTION

In a broad first aspect, the invention provides a nebuliser cup with a liquid level sensor comprising:
  a first element sensing liquid at or below a position corresponding to a filled liquid level in the nebuliser cup;
  a second element electrically isolated from the first element and located at a position corresponding to a filled liquid level in the nebuliser cup; and wherein
  when the cup is not filled with a liquid to the filled liquid level, the first element, the liquid and the second element do not form an electrically coupled circuit; and
  when the cup is filled with a liquid to the filled liquid level, the first element, the liquid and the second element together form an electrically coupled circuit.

The liquid is generally aqueous based, for example aqueous hydrogen peroxide.

The first and second elements may be independently selected from electrically resistive and electrically capacitive sensors.

The first and second elements may be resistive; or the first sensing element is resistive and the second sensing element is capacitive; or the first sensing element is capacitive and the second sensing element is resistive; or the first and second sensing elements are capacitive.

The element can pass through an insulated aperture in the cup wall, preferably the insulated aperture in the cup wall is an aperture surrounding an insulating sleeve.

In one embodiment, the first element is the nebuliser cup, such as an electrically conducting plastic cup, metal cup, or a non-conducting cup incorporating an electrically conductive element not in direct contact with the liquid.

According to a second aspect the invention provides a nebuliser cup with a liquid level sensor comprising:

an electrically conducting nebuliser cup and a conductive sensor electrically insulated from the cup and positioned such that when the cup is filled with a liquid to be nebulised, the cup, liquid and the conductive sensor together form an electrically coupled circuit.

The electrically conducting nebuliser cup may be a metal cup (for example, aluminium or stainless steel) or an electrically conducting plastic cup.

The sensor is a conductive level sensor.

Preferably, the sensor is located at a position corresponding to a filled liquid level in the electrically conducting nebuliser cup.

In one preferred embodiment, the sensor passes through an insulated aperture in the cup wall. The insulated aperture in the cup wall may be an aperture surrounding an insulating sleeve.

Preferably the insulating sleeve extends beyond the wall of the cup to a distance such that a droplet of liquid is unable to complete a circuit with the sensor and the cup.

In a third aspect, the invention provides a nebuliser cup with a liquid level sensor according to the preceding aspect in combination with a feedback loop and a liquid filling reservoir.

In a fourth aspect the invention relates to a method of maintaining a liquid level in a nebuliser cup during operation, the method comprising:

providing a first element at or below a position corresponding to a filled liquid level in a nebuliser cup;

providing a second element electrically isolated from the first element to contact a liquid at a position corresponding to a filled liquid level in the nebuliser cup;

providing sufficient liquid to the nebuliser cup to reach said fill level thereby to complete an electrically coupled circuit between the first element, the liquid and the second element;

and whereby a drop in the liquid level to below the fill level triggers a break in the circuit between the first element, the liquid and the second element; and whereby the break in the circuit triggers dispensation of further liquid in the nebuliser cup.

Figure 6:
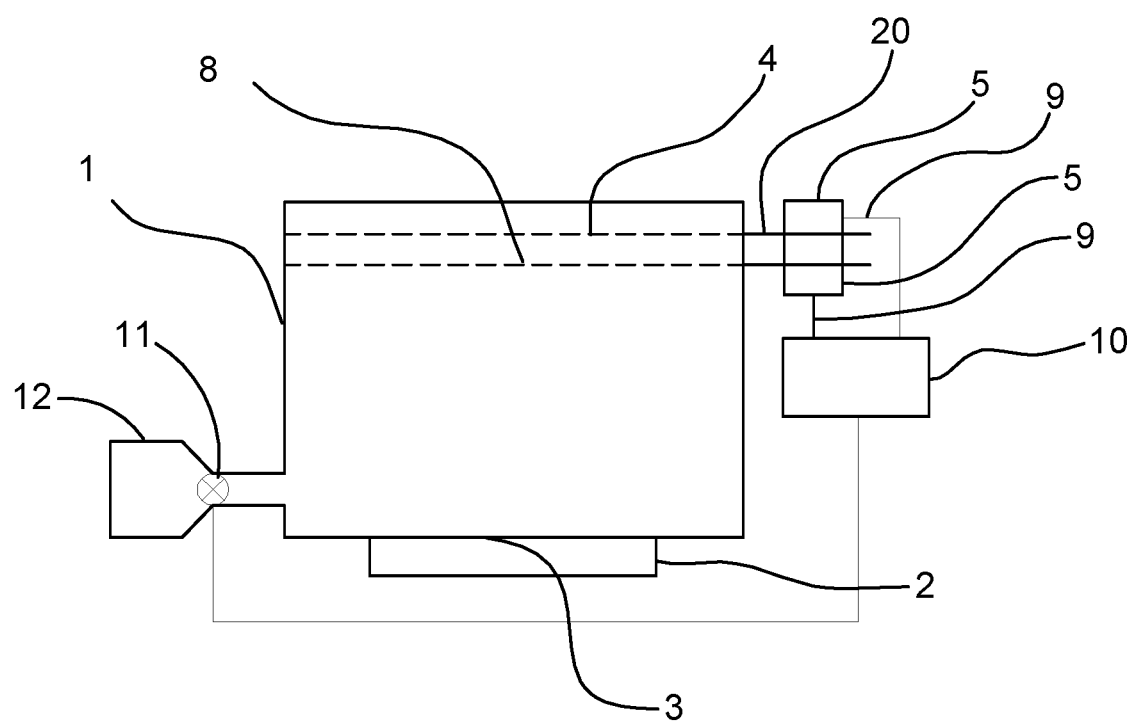

According to a fifth aspect the invention provides a method of maintaining a liquid level in a nebuliser cup during operation comprising:

positioning a conductive sensor at fill level relative to a conductive nebuliser cup, said conductive sensor being electrically insulated from the conductive nebuliser cup;

providing sufficient liquid to conductive nebuliser cup to reach said fill level thereby to complete a circuit between the cup, the liquid and the sensor;

and whereby a drop in the liquid level to below the fill level triggers a break in the circuit between the cup, the liquid and the sensor; and whereby in turn the break in the circuit triggers dispensation of further liquid in conductive nebuliser cup.

Preferably sufficient further liquid is dispensed to the conductive nebuliser cup in response to the break in the circuit to restore the circuit and halt further dispensation of liquid into the reservoir.

In one embodiment, the break in the circuit triggers dispensation of further liquid in the reservoir immediately. Such an embodiment could be used in the case where the liquid was dispensed to the cup whilst ultrasonic nebulization was in progress.

In an alternative embodiment, the break in the circuit triggers dispensation of further liquid in the reservoir after or at a predetermined time. That particular embodiment could be used where the liquid was dispensed to the cup whilst ultrasonic nebulization was not in progress, i.e. where discrete non-overlapping nebulization and liquid level sensing periods are employed. In such a case, sensing of the liquid level may occur prior to a nebulization period, or may occur after a predetermined period of nebulization has concluded. In each case, the determination of the liquid level would either result in a dispensation of liquid to the nebuliser cup or termination of the process (if the liquid level was below the sensing threshold) or would result in the process continuing (if the level was above the sensing threshold).

In a sixth aspect, the invention provides a nebuliser cup according to the first aspect in operative contact with an ultrasonic transducer.

In a seventh aspect, the invention provides a nebuliser cup according to the first or the fifth aspect located in fluid communication with a sterilizing chamber.

The liquid used for sterilization is preferably hydrogen peroxide solution or peracetic acid solution.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

Unless explicitly stated otherwise, conductive and conduction is used interchangeably, incorporating both AC and DC electrical current flow.

In the present invention, the nebuliser cup has a base, an upwardly extending wall and an open top whereby nebulised mist can be generated directly from bulk liquid contained, in use, within the cup. An ultrasonic transducer is preferably located at or adjacent to the base of the nebuliser cup or, alternatively, the ultrasonic transducer defines at least a portion of the base of the nebuliser cup. In the latter case the ultrasonic transducer acts directly upon the liquid in the cup, at the base, to apply ultrasonic energy to the liquid in the cup, thereby resulting in generation of an aerosol from the surface of the liquid. One face only of the ultrasonic transducer is in contact with, or transmissive to the liquid in the cup, and the liquid in the cup does not pass through the transducer.

DESCRIPTION OF THE DRAWINGS

FIG. 1 shows a schematic diagram of the nebuliser cup of the present invention.

FIGS. 2 and 3 show a preferred nebuliser cup of the present invention.

FIG. 4 is an assembly view of a preferred nebuliser cup of the present invention in its operating environment.

FIGS. 5*a* and 5*b* show alternative embodiments of the invention

FIG. 6 shows yet another embodiment of the invention.

DESCRIPTION OF THE INVENTION

The present invention provides a nebuliser cup which allows for detection of liquid level in the cup whilst being of sufficiently simple and robust design to withstand harsh environments such as may be found within ultrasonic sterilizing apparatus.

The general principle of the device is that at least one of the sensor elements is positioned at an "upper" fill level position and the other at or below the fill position, which may be called a "lower" position (although both sensors may be at the fill position, as long as isolated from each other when liquid is absent). When the cup is filled with liquid, the upper sensor element, the lower sensor element and the liquid form a circuit. When the liquid is consumed, the upper level of the liquid drops below the upper sensor, breaking the circuit, which in turn triggers the dispensation of additional liquid to refill the cup.

The sensors can either the same or different, and can be either capacitive or conductive. The options are shown below in Table 1.

TABLE 1

| Option | Sensor 1 (at or below fill level) | Sensor 2 (at fill level) |
| --- | --- | --- |
| 1 | Direct electrical contact with fluid | Direct electrical contact with fluid |
| 2 | Capacitive contact with fluid | Direct electrical contact with fluid |
| 3 | Direct electrical contact with fluid | Capacitive contact with fluid |
| 4 | Capacitive contact with fluid | Capacitive contact with fluid |

The apparatus is described with respect to the drawings, in which the sensors are both conductive, and in which one of the sensors, that at or below fill level, is the cup itself.

Nebuliser cup 1 is in operative engagement with ultrasonic transducer 2. The transducer is in contact with the base 3 of the cup, 3. Operation of transducer 2 serves to ultrasonicate liquid, where present, in cup 1. The liquid in the cup, typically containing aqueous hydrogen peroxide, is advantageously filled at least to fill level 4. As transducer 2 operates and the liquid is ultrasonicated and converted to a nebulant, which is dispersed, the upper level of the liquid drops. As the level of the liquid drops, the nebulization process can become sub optimal, and on approaching very low liquid levels, the liquid may be unable to disperse the ultrasonic energy, and the transducer 2, can begin to heat, with possibly destructive consequences.

The present invention includes a sensor 5 which is positioned at the fill level 4. The fill level can be chosen to achieve the optimal liquid level height given the other operating parameters of the device. In this case, the positioning is achieved by way of an aperture 6 in the cup 1, into which is placed sensor 5 surrounded by an isolating sleeve 7. The isolating sleeve may be of any suitable material, for example, chemically resistant PVDF (polyvinylidene fluoride), PEEK, PTFE etc.

Ideally, the sensor at or below fill level is configured to switch on the pump or open the valve so as to introduce more liquid into the nebuliser cup (or switch off the transducer, if the reservoir is empty) when the level of liquid in the nebuliser cup falls to a predetermined level. In preferred embodiments, that predetermined level is at least 5 mm from the base of the cup or surface of the transducer. That, is, the lower liquid level sensor is positioned at 5 mm or greater from the base of the cup so that the cup will always retain a minimum of 5 mm depth in the base of the cup to ensure that there is sufficient liquid present to absorb ultrasonic energy and prevent the transducer from destructive delamination.

The typical diameter of the nebuliser cup, based upon the sizing of most ultrasonic transducers, is at least around 20 mm, so the fill sensors are typically positioned such that the liquid does not fall below a minimum volume of 1.5 cm$^3$ of liquid.

Whilst the main purpose of the present invention is to protect the nebuliser from running dry, the nebuliser cup of the present invention also allows the setting of upper and lower sensor levels to determine optimum performance of the nebuliser. The ultrasonic transducer focuses energy into the cup, causing a mist of droplets to arise. In some cases, the mist and droplet profile can vary depending upon whether the mist is generated from a full cup or from a cup with a lower liquid level. The upper and lower sensor levels can be determined, based on the transducer and cup design, so as to bracket the optimum liquid level. This means that in use, the nebuliser cup of the present invention can provide a mist that it consistently around the optimum achievable.

The sensor is an AC excited coupled liquid level sensor. The excitation signal may be of any suitable form, for example, a 5 Vp-p 6 kHz square wave and is coupled via a capacitor to the sensor electrode. This ensures that there is no DC potential on the sensor electrode; avoiding any problems with electrolysis of the liquid.

When the liquid level is at the fill level 4, it contacts the sensor 5. The sensor has an aluminium, or stainless steel, sensor pin 5a which contacts the liquid where present. There is a drop in the electrode signal level that occurs when the $H_2O_2$ level in the cup is high enough to contact the electrode. This shunts some of the signal to earth via the conductive path formed between the sensor and the earthed metallic cup.

When the apparatus is in use, the liquid in the cup is consumed as a result of the nebulisation process, and the liquid level falls. At some time, the liquid level will drop to a sub-fill level 8. At this level, pin 5a will no longer contact the liquid and sensor 5 will stop sensing it, and that information will be fed via pathway 9 into controller 10.

If controller 10 detects a low electrode signal below a predetermined threshold, then it infers sufficient liquid is present in the cup. If controller 10 detects a high electrode signal, above a predetermined threshold, then it infers insufficient liquid is present in the cup.

In the case of insufficient liquid level detected by sensor 5, controller 10 triggers the opening of valve 11 which permits additional liquid to flow from reservoir 12 into cup 1, either under gravity or by pumping. Alternatively, a peristaltic pump could be used at 11 to close reservoir 12 when not pumping.

Controller 10 can be configured to trigger the release of a liquid either immediately upon detection of a fall in liquid level, or at a predetermined time after a fall in liquid level is detected, usually a few seconds, during which time the liquid level will fall below the sub-fill level 8, but not so much as to reach the base of the cup. In this way a safe and operationally useful liquid level is maintained. Importantly, the sensor is sized and positioned such that liquid droplets such as nebulant particles or particles of condensate are unable to complete the circuit between the sensor and the conducting cup, thereby generating a false signal that would result in destruction of the apparatus. Additionally, the positioning of the sensor and the triggering of additional liquid can be configured to take into account meniscus formation. One such example would be an insulating sheath around the sensor to prevent electrical contact between the cup and the sensor. The insulating sheath preferably provides around a 1 mm or greater gap between the sensor and the conducting cup.

Because the switching is qualitative ("on-off") rather than quantitative, it is more robust and less prone to error or the need for recalibration. Also, because of the large difference between on and off voltages, the system can readily operate over a large range of sterilization liquids without recalibration or standardization.

Additionally, the cup can be used in apparatus where the nebulization and dispensation of liquid to the cup (refilling) occur either simultaneously or sequentially. For example, in larger apparatus, nebulization may take place continuously, and filling would then take place as needed while nebulization was on going, so as to maintain the predetermined liquid level. However, in other embodiments, nebulization takes place on an intermittent basis, and it may in those cases be advantageous to conduct sensing of the liquid levels whilst nebulization is off. For example, sensing can take place before nebulization commences, or between nebulization intervals. In that case, if insufficient levels are detected, the nebulizer cup is refilled before nebulization recommences.

It may be desirable in some cases to overfill the nebulizer above the fill level. In that case, a further overfill sensor at a higher level can be used to detect an overfill condition. Alternatively, the overfill level could be determined by the refilling liquid volumetric flow rate and a time delay between the detection of liquid and the cessation of refilling.

The lower level may also be selected so that it can accommodate a further predetermined time interval prior to switching off the transducer or introducing more liquid.

The cup may be made from any type of conducting material, for example, a metal such as aluminium or alternatively, the cup maybe made from a conducting plastic. In an alternative embodiment, the cup is not made from a conducting material, but instead has an appropriate conductive portion located inside the cup at fill level.

Figure 2:
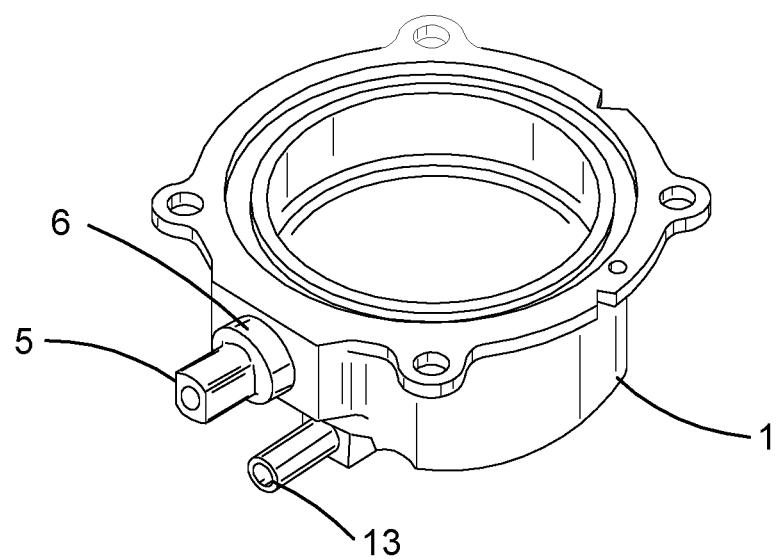
Figure 3:
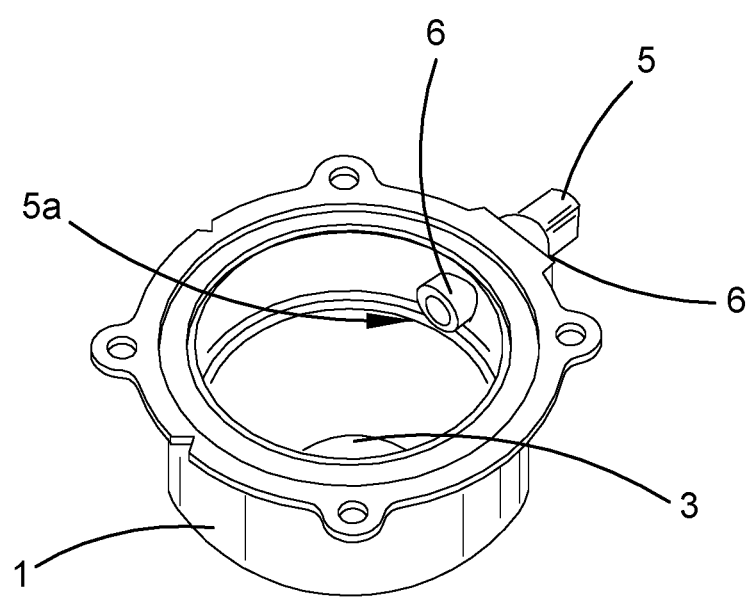
Figure 4:
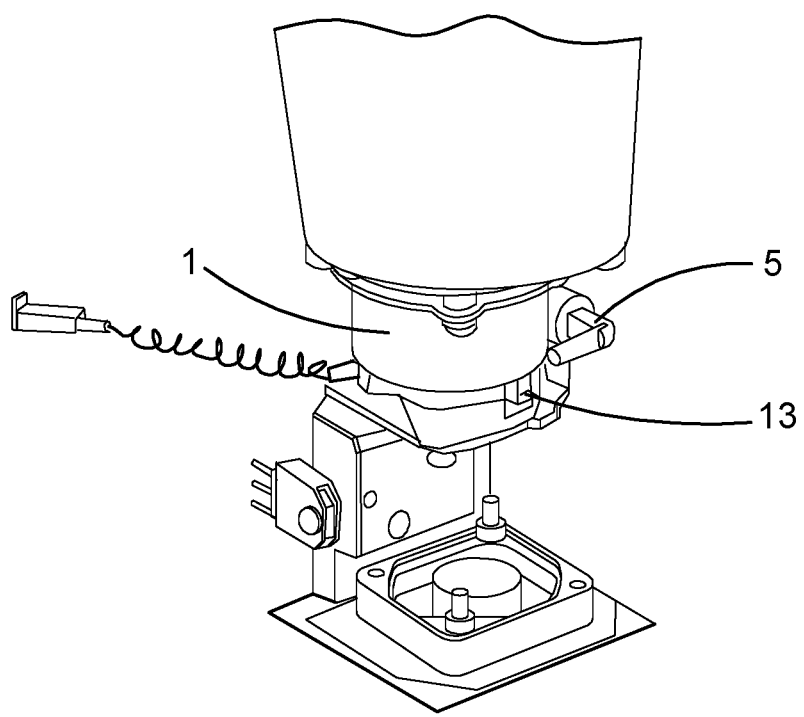

A further embodiment of the device is shown in FIGS. 2 and 3. Cup 1 can be tapered towards the bottom if desired. The reservoir in this apparatus can be seen to fill via port 13 which is at the bottom of the reservoir. FIG. 4 is an assembly view.

Figure 5A:
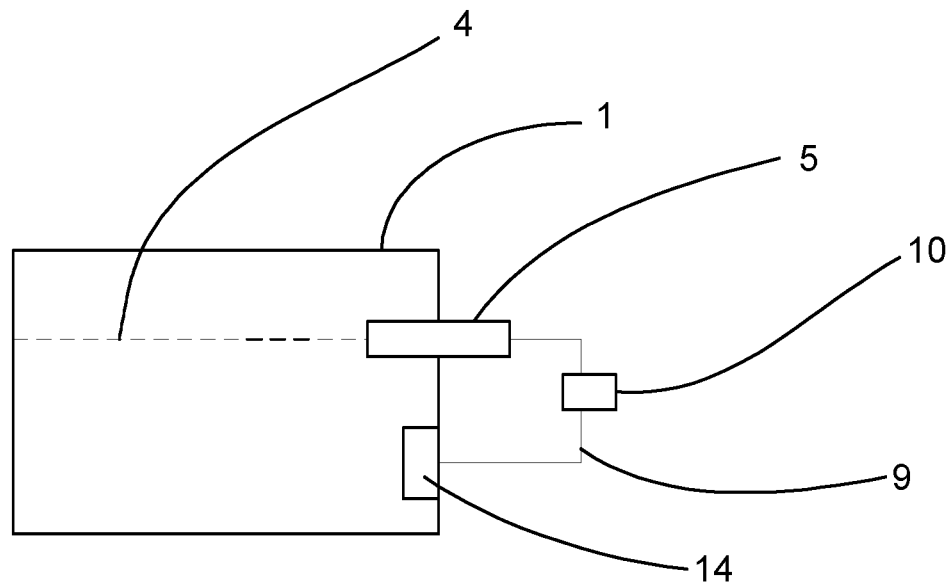
Figure 5B:
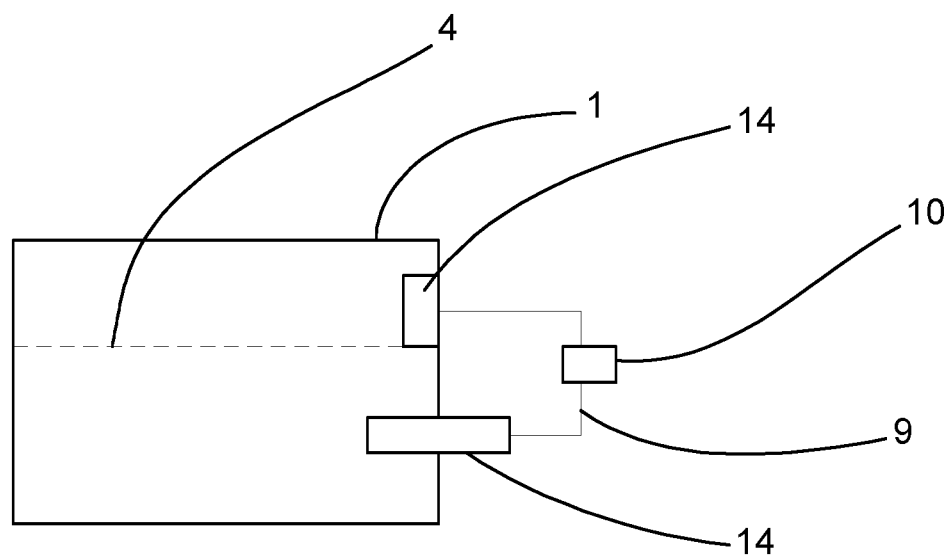

FIGS. 5a and 5b show alternative embodiments of the invention. In this case, the cup 1 is not conductive, but rather the circuit is completed by way of a sensor element (e.g. an electrode of some type) which completes the circuit only when the liquid is at a fill level 4.

A further embodiment is shown in FIG. 6. In this case the liquid level sensors 5 are located away from the cup body 1 but are in fluid communication with the liquid in the cup and are located at a level corresponding to the fill level 4 of the cup.

When the apparatus is in use, the liquid in the cup is consumed as a result of the nebulisation process, and the liquid level falls. At some time, the liquid level will drop to a sub-fill level 8. At this level, liquid no longer remains in exit pipe 20, which has sensors 5 located along it at level corresponding to fill level 4. The sensors 5 fail to sense the presence of liquid, leading to an increase in signal, controller 10. The sensors then sense the presence of liquid in the exit pipe which in turn leads controller 10 to infer there is insufficient liquid is present in the cup. Controller 10 then triggers the opening of valve 11 which permits additional liquid to flow from reservoir 12 into cup 1, either under gravity or by pumping. Alternatively, a peristaltic pump could be used at 11 to close reservoir 12 when not pumping.

Controller 10 can be configured to trigger the release of a liquid either immediately upon detection of a fall in liquid level, or at a predetermined time after a fall in liquid level is detected, usually a few seconds, during which time the liquid level will fall below the sub-fill level 8, but not so much as to reach the base of the cup. In this way a safe and operationally useful liquid level is maintained.

Additionally, as mentioned, it is not necessary that either or both of the sensors are conductive. Either or both of the sensors may be capacitive. A capacitive sensor has plates which are not in direct conduct with the liquid, but is physically separated by way of a barrier layer but is nevertheless electrically coupled to it. Typically, a capacitive sensor would be present on the outside of the cup, or placed inside the cup wall material, which forms a barrier layer. When the liquid comes into contact with the barrier layer adjacent the capacitive sensor, an AC current is able to flow if the circuit is otherwise complete (e.g. by way of another sensor element either directly in contact with the liquid or in capacitive contact with the fluid).

In the case of direct sensors, the current can be either AC or DC, although DC is not preferred as it can lead to electrolysis of the liquid. In the case of capacitive sensors, or mixed capacitive/conductive sensors, AC is required.

The invention claimed is:

1. A method of maintaining a liquid level in a nebuliser cup in a sterilisation apparatus during operation, the method comprising:
    providing a first element sensing liquid at or below a position corresponding to a filled liquid level in the nebuliser cup;
    providing a second element electrically isolated from the first element to contact a liquid at a position corresponding to the filled liquid level in the nebuliser cup;
    providing sufficient liquid to the nebuliser cup to reach said filled liquid level thereby to complete an electrically coupled circuit between the first element, the liquid and the second element;
and
    whereby a drop in the liquid level to below the filled liquid level triggers a break in the circuit between the first element, the liquid and the second element; and
    whereby the break in the circuit triggers dispensation of further liquid in the nebuliser cup,
    wherein the sterilisation apparatus comprises a sterilisation chamber, an inlet valve an outlet valve, an ultrasonic nebuliser in fluid communication with the chamber via the inlet valve, and a fan upstream of and in fluid communication with the ultrasonic nebuliser during operation, and
    wherein the nebuliser cup comprises a base, an upwardly extending wall, and an open top, whereby an aerosol can be generated directly from the liquid in the nebuliser cup wherein the open top is free of a cover, wherein the cover would prevent flow of the aerosol out of the open top; and wherein nebulization takes place on an intermittent basis and wherein sensing of the liquid levels is conducted when nebulization is off.

2. A method according to claim 1 wherein sufficient further liquid is dispensed to the nebuliser cup in response to the break in the circuit to restore the circuit and halt further dispensation of liquid from a reservoir.

3. A method according to claim 2 wherein the break in the circuit triggers dispensation of further liquid from the reservoir immediately.

4. A method according to claim 2 wherein the break in the circuit triggers dispensation of further liquid from the reservoir after a predetermined time.

5. A method according to claim 1 wherein the liquid used for sterilisation comprises a hydrogen peroxide solution or peracetic acid solution.

6. A method according to claim 1 wherein the first element at or below the filled liquid level is configured to maintain at least 5 mm depth of liquid in the nebuliser cup.

7. A method according to claim 1 wherein the first element at or below the filled liquid is configured to switch off a transducer when a volume of liquid in the nebuliser cup falls to about at least 1.5 $cm^3$.

8. A method according to claim 1 wherein the nebuliser cup is in fluid communication with a sterilisation chamber.

9. A method according to claim 1 wherein the first element is a non-conducting cup incorporating an electrically conductive element not in direct contact with the liquid.

10. A method according to claim 1 wherein sensing takes place before nebulisation commences.

11. A method according to claim 1 wherein sensing takes place between nebulisation intervals.

12. A method according to claim 1 wherein, if insufficient levels are detected, the nebuliser cup is refilled before nebulisation recommences.

13. A method according to claim 1 wherein the nebuliser cup is in operative contact with an ultrasonic transducer.

14. A method according to claim 1 wherein the nebuliser cup has an ultrasonic transducer at the base.

* * * * *